(12) United States Patent
Sobhy et al.

(10) Patent No.: US 10,441,671 B2
(45) Date of Patent: Oct. 15, 2019

(54) DISINFECTING APPARATUS

(71) Applicant: S and M Technology, LLC, Oak Lawn, IL (US)

(72) Inventors: Shawki Sobhy, Oak Lawn, IL (US); Horace Rodriguez, Schaumburg, IL (US); Gerald Vaagen, Palatine, IL (US)

(73) Assignee: S and M Technology LLC, Oak Lawn, IL (US)

(*) Notice: Subject to any disclaimer, the term of this patent is extended or adjusted under 35 U.S.C. 154(b) by 305 days.

(21) Appl. No.: 15/362,034

(22) Filed: Nov. 28, 2016

(65) Prior Publication Data

US 2017/0100498 A1    Apr. 13, 2017

Related U.S. Application Data

(63) Continuation-in-part of application No. 14/823,171, filed on Aug. 11, 2015, now Pat. No. 9,561,296.

(51) Int. Cl.
*A61L 2/22* (2006.01)
*A61L 2/10* (2006.01)
*B01D 46/00* (2006.01)
*A61L 2/18* (2006.01)

(52) U.S. Cl.
CPC ............... *A61L 2/22* (2013.01); *A61L 2/10* (2013.01); *B01D 46/0036* (2013.01); *B01D 46/0038* (2013.01); *A61L 2/18* (2013.01); *A61L 2202/122* (2013.01); *B01D 2275/40* (2013.01); *B01D 2279/35* (2013.01); *B01D 2279/55* (2013.01)

(58) Field of Classification Search
CPC ......... A61L 2/22; A61L 2/10; B01D 46/0038; B01D 46/0036
See application file for complete search history.

(56) References Cited

U.S. PATENT DOCUMENTS

| | | | |
|---|---|---|---|
| 5,035,367 A * | 7/1991 | Nojima .................. | A61L 11/00 241/37.5 |
| 5,413,089 A * | 5/1995 | Andors .................. | F24B 1/026 110/210 |
| 6,884,392 B2 * | 4/2005 | Malkin .................. | A61B 1/123 134/198 |
| 6,923,851 B1 * | 8/2005 | Butler ................... | B01D 46/0023 55/324 |
| 2003/0124025 A1 * | 7/2003 | Mize ...................... | A61L 2/18 422/28 |
| 2008/0240981 A1 * | 10/2008 | Berentsveig .......... | A01N 25/06 422/29 |

* cited by examiner

*Primary Examiner* — Regina M Yoo
(74) *Attorney, Agent, or Firm* — Rockman Videbeck & O'Connor

(57) ABSTRACT

A disinfecting apparatus for cleaning, disinfecting, and sanitizing a wide variety of devices used by medical personnel, law enforcement and correctional facilities, body art establishments, and the like, comprises a top portion, an upper portion that includes a main tank, and a lower portion that includes a water pump and reservoir tank. The water pump conveys the disinfectant solution from the main tank through a filter to the piping system that delivers the disinfectant solution to the plurality of jets that dispense the disinfectant solution to the devices held on a removable holding device within the interior chamber. The devices are then further sanitized and sterilized by a blower and UV-C light exposure.

21 Claims, 18 Drawing Sheets

Gate sensor limit switch motor encoder sensor switch

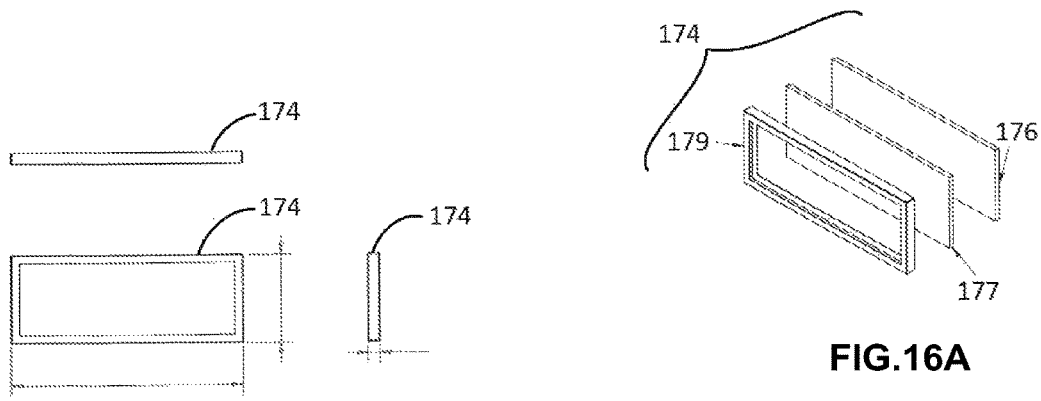
FIG.16A
FIG.16B
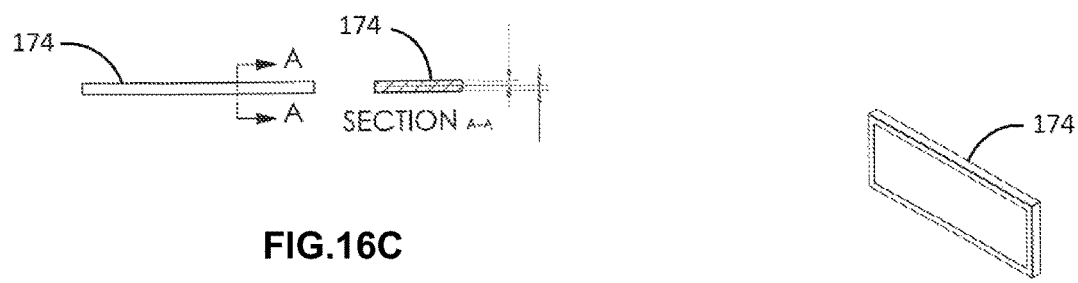
FIG.16C
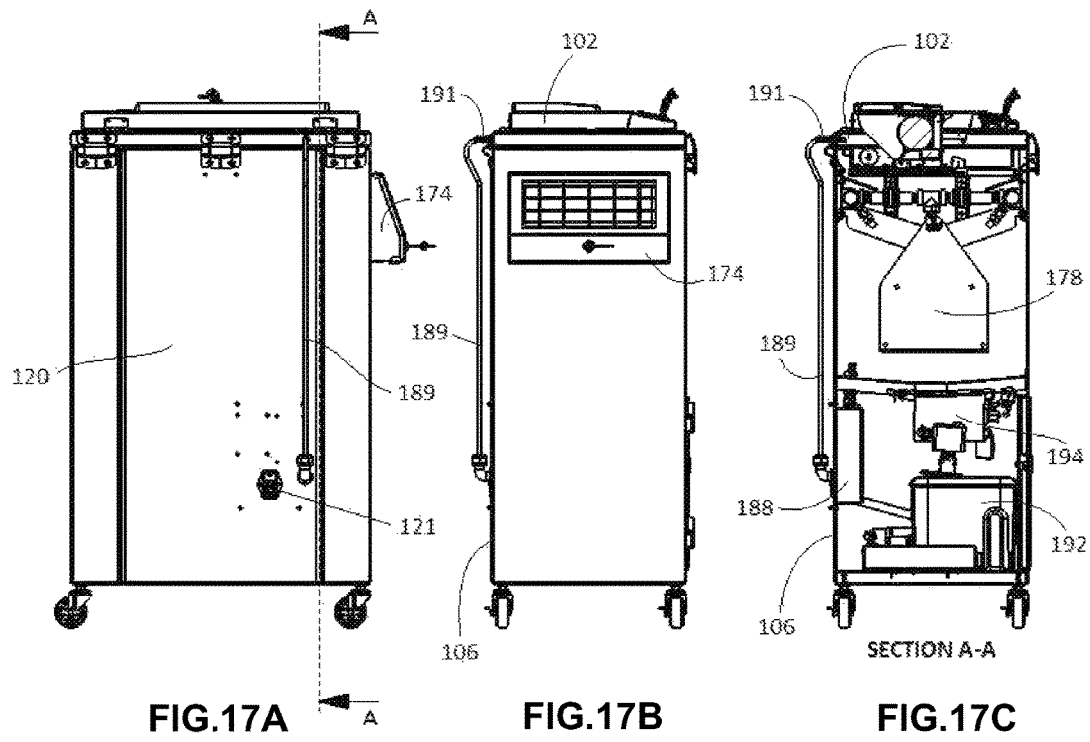
FIG.17A   FIG.17B   FIG.17C

DISINFECTING APPARATUS

CROSS-REFERENCE TO RELATED APPLICATION(S)

This application claims priority to and is a continuation-in-part of U.S. Non-provisional application Ser. No. 14/823,171, filed Aug. 11, 2015, to the extent allowed by law and the contents of which are incorporated herein by reference in their entireties.

TECHNICAL FIELD

This disclosure relates to a disinfecting apparatus.

BACKGROUND

A wide variety of items and devices used in various fields, whether for personal use or professional use, are required to be cleaned, disinfected, and/or sanitized routinely or between each use of the item or device. For example, law enforcement and correctional facilities utilize a wide variety of restraining devices such as handcuffs, shackles, and chains, to restrain individuals in their custody. The handcuffs, shackles, and chains make contact with the skin of the individual being restrained and with the skin of the law enforcement personnel applying the handcuffs, shackles, and chains. Over time, the restraining devices become dirty and can become contaminated with dirt, bacteria, and disease. The restraining devices must be routinely cleaned, disinfected, and sanitized in order to prevent contamination and the spread of bacteria and disease. Medical personnel and facilities use a wide variety of instruments during patient examinations and surgical procedures that must be routinely cleaned, disinfected, and sanitized after each use. Tattoo artists and piercing establishments use instruments that must also be cleaned, disinfected, and sanitized after each use. The disinfecting apparatus of the present disclosure is designed to clean, disinfect, and sanitize a plurality of devices in a sealed chamber using a disinfectant solution, short-wavelength ultraviolet (UV-C) light, and a blower, eliminating the need for plumbing, drainage, or a backflow prevention device. The disinfecting apparatus of the present disclosure may also utilize a standard disinfectant solution as well.

SUMMARY

This disclosure relates generally to a disinfecting apparatus. One implementation of the teachings herein is a disinfecting apparatus that includes an upper portion comprising a compartment that defines an interior chamber, the upper portion having a top portion in moveable communication with the upper portion, the top portion configured to alternately open and close access to the interior chamber; an upper door in moveable communication with the compartment, the upper door configured to alternately open and close access to the interior chamber; a plurality of jets disposed in the upper portion, the plurality of jets configured to convey a disinfectant solution to the interior chamber; a lower portion subjacent the upper portion, the lower portion comprising a lower door, a lower chamber, a rotatable tray, and a water pump configured to convey the disinfectant solution to each jet of the plurality of jets located on the pressurized wall with an equal pressure to each jet, the lower door in moveable communication with the lower portion, the lower door configured to alternately open and close access to the lower chamber.

These and other aspects of the present disclosure are disclosed in the following detailed description of the embodiments, the appended claims and the accompanying figures.

BRIEF DESCRIPTION OF THE DRAWINGS

The various features, advantages, and other uses of the apparatus will become more apparent by referring to the following detailed description and drawings, wherein like reference numerals refer to like parts throughout the several views. It is emphasized that, according to common practice, the various features of the drawings are not to-scale. On the contrary, the dimensions of the various features are arbitrarily expanded or reduced for clarity.

FIG. 16A is an exploded perspective view of a filtration system used in the upper portion of the second embodiment of the disinfecting apparatus;

FIG. 16B is a perspective view of the filtration system used in the upper portion of the second embodiment of the disinfecting apparatus;

FIG. 16C are elevation views of the filtration system used in the upper portion of the second embodiment of the disinfecting apparatus, showing the dimensions of the filtration system in this particular second embodiment of the disinfecting apparatus;

FIG. 17A is a rear elevation view of the second embodiment of the disinfecting apparatus, showing a female electrical connector;

FIG. 17B is a first side elevation view of the second embodiment of the disinfecting apparatus, showing a strain relief on the rear of the top portion attached to a connector extending to the lower portion;

FIG. 17C is a first side cross-sectional view, along line A-A of FIG. 17A, of the second embodiment of the disinfecting apparatus, showing the connector extending from the strain relief on the rear of the top portion to the rear of the lower portion;

FIG. 20 is a second side cross-sectional perspective view of the top portion of the second embodiment of the disinfecting apparatus, showing a blower and the UV-C light door in the open position with a plurality of UV-C lights turned on.

DETAILED DESCRIPTION

Figure 1:
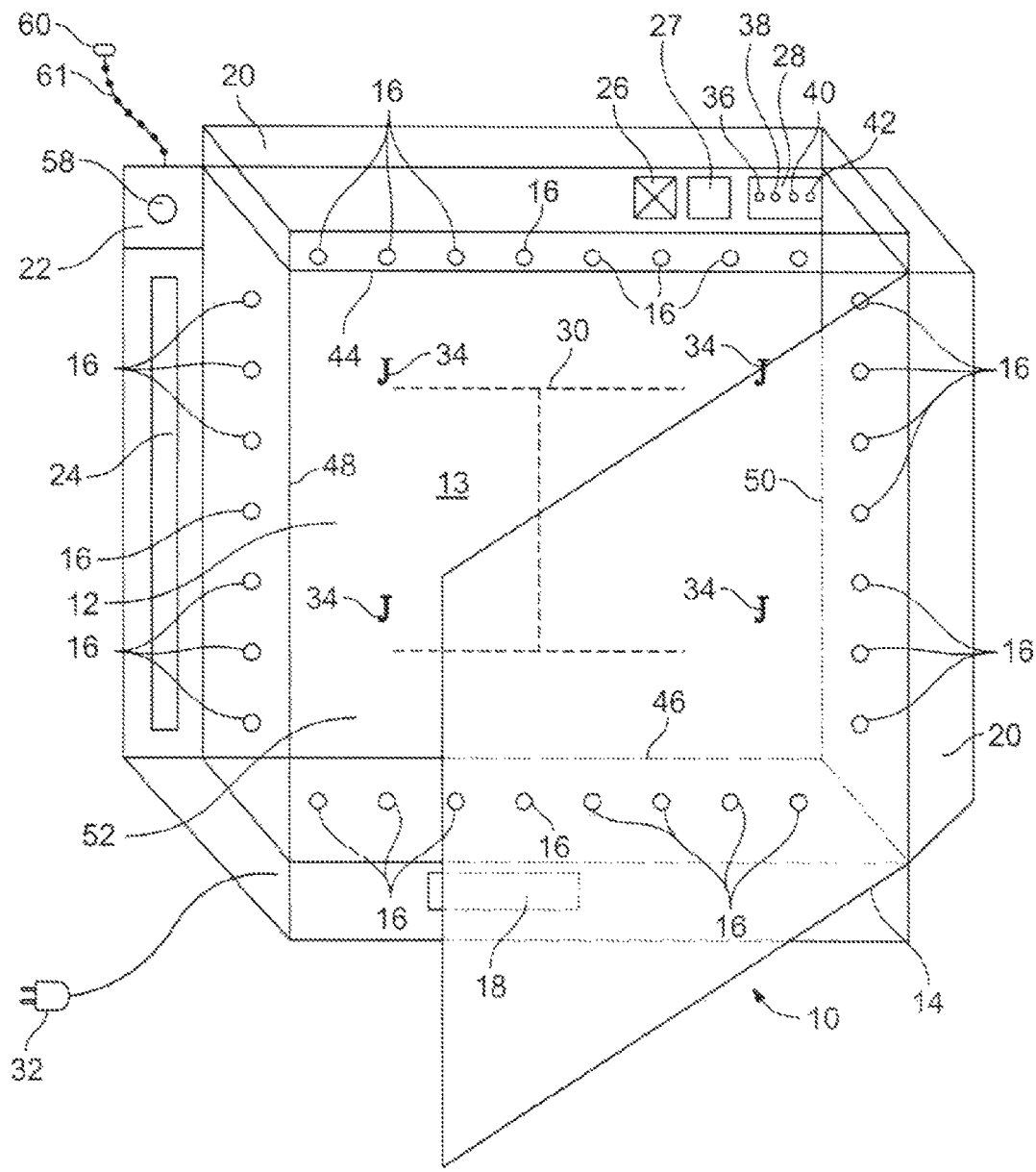
FIG. 1 is a front perspective view of a first embodiment of a disinfecting apparatus, showing a transparent door.

A wide variety of items and devices used in various fields, whether for personal use or professional use, are required to be cleaned, disinfected, and/or sanitized routinely or between each use of the item or device. For example, law enforcement and correctional facilities utilize a wide variety of restraining devices such as handcuffs, shackles, and chains, to restrain individuals in their custody, medical personnel and facilities use a wide variety of instruments during patient examinations and surgical procedures, tattoo artists and piercing establishments use instruments to create body art and attach body piercings on individuals, and the general public has several household items that they may want routinely cleaned, disinfected, and/or sanitized. The handcuffs, shackles, and chains make contact with the skin of the individual being restrained and with the skin of the law enforcement personnel applying the handcuffs, shackles, and chains. The medical and surgical instruments used on patients make contact with the patient, the medical staff, and bacteria, viral, and other contaminants. The instruments used by body art personnel also come in contact with bacteria and contaminants from the customers, the professional body art artists, and the environment they instruments are used in. Additionally, items used in everyday life, such as cooking, serving, and cooking items and utensils come into contact with human as well as food-based contaminants. These instruments and devices, just to name a few, become dirty and contaminated with dirt, bacteria, and disease. The instruments and devices must be cleaned and disinfected in order to prevent contamination and the spread of bacteria and disease. The disinfecting apparatus of the present disclosure is designed to clean, disinfect, and sanitize a plurality of devices in a sealed chamber using a disinfectant solution, short-wavelength ultraviolet (UV-C) light, and a blower, reducing or eliminating atmospheric contamination and biohazard residue.

A first embodiment of the disinfecting apparatus of the present disclosure is particularly designed to allow the disinfectant solution to substantially evaporate, thereby eliminating the need for plumbing, drainage, or a backflow prevention device. The disinfecting apparatus of this first embodiment comprises a compartment that includes an interior chamber and a door, a disinfectant chamber for retaining a disinfectant solution, a plurality of jets, at least one plenum, a water pump for conveying the disinfectant solution from the disinfectant chamber to the compartment through the plurality of jets, a power switch, and an electrical power plug to electrically connect the disinfecting apparatus to a power supply. The compartment includes a top wall, a bottom wall, a first side wall, a second side wall, and a rear wall having a first side and a second side opposite the first side. The plurality of jets is disposed in at least one of the top wall, bottom wall, first side wall, and second side wall of the compartment. The plenum is located on at least one of the top wall, bottom wall, first side wall, and second side wall of the compartment, each plenum connecting the plurality of jets on that particular wall and evening out the pressure applied to each jet. The plurality of jets conveys the disinfectant solution in a pulsed spray or a continuous mist spray to the devices within the interior chamber of the compartment.

The first embodiment, shown in FIG. 1, of a disinfecting apparatus 10 of the present disclosure comprises a compartment 12 that defines an interior chamber 13 and includes a door 14, a plurality of jets 16, a water pump 18, at least one plenum 20, a disinfectant chamber 22 in communication with compartment 12, and an electrical power plug 32. The water pump 18 conveys a disinfectant solution from the disinfectant chamber 22 to compartment 12 through the plurality of jets 16. The compartment 12 includes a top wall 44 opposite a bottom wall 46, a first side wall 48 opposite a second side wall 50, and a rear wall 52 having a first side and a second side opposite the first side. The plurality of jets 16 are disposed in at least one of the top wall 44, the bottom wall 46, the first side wall 48, and the second side wall 50 of compartment 12. The plenum 20 is located on at least one of the top wall 44, bottom wall 46, first side wall 48, and second side wall 50 of compartment 12. The plenum 20 connects to the plurality of jets 16 located on that particular wall of compartment 12 in which the plenum 20 is located and the plenum 20 is adapted to even out the pressure to each jet in the plurality of jets 16 on that particular wall. The plurality of jets 16 conveys the disinfectant solution in a pulsed spray or a continuous mist spray to the devices within interior chamber 13 of compartment 12. The plurality of jets 16 can also include stainless steel tips.

The first side of rear wall 52 of compartment 12 includes a plurality of support structures 34, such as hooks, adapted to hold at least one device (not shown) per support structure 34 within interior chamber 13 and allowing the disinfecting apparatus 10 to potentially clean a plurality of devices at one time. The rear wall 52 further includes a mounting system 30, located on the second side of rear wall 52 opposite the first side that includes the plurality of support structures 34, the mounting system 30 securing the disinfecting apparatus 10 to a vertical, planar surface.

The top portion of compartment 12 includes a power switch 26, a start button 27, and a light indicator panel 28 disposed on plenum 20. The light indicator panel 28 includes at least one of a low liquid light indicator 36, an in-use light indicator 38, a ready light indicator 40, and a power light indicator 42. The low liquid light indicator 36 is illuminated when the disinfectant solution reaches a predetermined level within the disinfectant chamber 22. The in-use light indicator 38 is illuminated once the start button 27 is pressed and the disinfecting apparatus 10 is in a cycle of operation. The ready light indicator 40 is illuminated when the disinfecting apparatus 10 is ready to commence a cycle of operation. The power light indicator 42 is illuminated when the power switch 26 is in the ON position, the electrical power plug 32 is electrically connected to a power source, and the disinfecting apparatus 10 is receiving power from the power source.

Door 14 includes a sealing gasket (not shown) that forms an air tight seal between door 14 and compartment 12 when door 14 is closed and prevents the disinfectant solution from escaping from interior chamber 13 of compartment 12 into the atmosphere. Door 14 includes a sensor (not shown) that shuts off air compressor 18 to terminate the cycle of operation of disinfecting apparatus 10 when the sensor detects that door 14 is opened during the cycle of operation. In a modification of the first embodiment, door 14 can include a timer (not shown) that maintains door 14 closed and locked for a predetermined amount of time while the disinfecting apparatus 10 is in a cycle of operation. Once the cycle of operation completes and the timer expires, door 14 is unlocked and the user can open door 14. In yet another modification of the first embodiment, the disinfecting apparatus 10 can include an emergency kill switch (not shown) that allows a user to immediately shut off the disinfecting apparatus 10 in an emergency situation when the emergency kill switch is activated.

The disinfectant chamber 22 is adapted to retain a predetermined amount of disinfectant solution and includes a clear display 24 that indicates the amount of disinfectant solution remaining within the disinfectant chamber 22. The disinfectant chamber 22 includes an aperture 58 allowing access to the interior of the disinfectant chamber 22 and a removable cover 60 closing access to the interior of the disinfectant chamber 22 when removable cover 60 engages aperture 58. The removable cover 60 is connected to the disinfectant chamber 22 through a chain 61 or similar means. In one modification of the first embodiment, cover 60 includes one of a plug having a sealing gasket and a screw cap. The disinfectant solution is poured into the disinfectant chamber 22 through aperture 58.

When the disinfecting apparatus 10 is in a cycle of operation, the disinfectant solution, under the force of water pump 18, is conveyed from disinfectant chamber 22 to the plurality of jets 16 to provide a pulsed spray or a continuous spray mist of disinfectant solution to the devices within interior chamber 13 of compartment 12 and suspended from the plurality of support structures 34. The disinfectant solution can be conveyed directly from the disinfectant chamber 22 to the plurality of jets 16 or can be conveyed from the disinfectant chamber 22, through plenum 20, and then to the plurality of jets 16. The disinfectant solution is only dispensed from disinfectant chamber 22 when door 14 is in the closed position and an air tight seal has formed between door 14 and compartment 12.

The disinfecting apparatus 10 is a plug and go apparatus that only requires the user to engage electrical power plug 32 with a power source for operation. To use disinfecting apparatus 10, the user places the devices upon support structures 34 within interior chamber 13 of compartment 12 and closes door 14, forming an air tight seal between compartment 12 and door 14. When power switch 26 is placed in the ON position and the start button 27 is pressed, the water pump 18 forces the disinfectant solution from disinfectant chamber 22 to the plurality of jets 16. Plenum 20 connects the plurality of jets 16 and ensures that the disinfectant solution is evenly dispensed from each jet 16. The disinfectant solution is dispensed from jets 16 in a pulsed spray or in a continuous spray mist onto the devices.

Water pump 18 is shut down to terminate the cycle of operation of disinfecting apparatus 10 if the sensor (not shown) has detected that door 14 has been opened prior to termination of the cycle of operation of the disinfecting apparatus 10. In the first embodiment of the present disclosure, the disinfectant solution substantially evaporates over a predetermined amount of time and the user can then open door 14. When the embodiment includes the timer (not shown), the timer maintains door 14 closed and locked for a predetermined amount of time while the disinfecting apparatus 10 is in a cycle of operation. Once the timer expires, door 14 is unlocked and the user can then open door 14. The disinfecting apparatus 10 and water pump 18 are also shut down to immediately terminate the cycle of operation of the disinfecting apparatus 10 if the emergency kill switch is activated in an emergency situation.

In yet a further modification of the first embodiment, the water pump 18 forces the disinfectant solution from disinfectant chamber 22 to the plurality of jets 16. The disinfectant solution is dispensed from jets 16 in a pulsed spray or in a continuous spray mist onto the devices within compartment 12. The water pump 18 subsequently forces the disinfectant solution through the plurality of jets 16 to assist in evaporating the disinfectant solution and drying the devices within compartment 12. A removable tray (not shown) is included below bottom wall 46 of compartment 12 to collect any remaining disinfectant solution that has not yet evaporated.

A second embodiment, shown in FIGS. 2-20, of a disinfecting apparatus 100 of the present disclosure comprises a top portion 102, an upper portion 104 subjacent the top portion 102, and a lower portion 106 subjacent the upper portion 104. The upper portion 104 comprises a compartment 108 that defines an interior chamber 110 and main tank 111 (FIG. 14B), both shown in skeletal view in FIGS. 3-5 and 8-12, that is accessible through an upper door 112, shown in FIGS. 2-5 and 8-11. The upper door 112 of upper portion 104 includes a sealing gasket (not shown) that forms an air tight seal between upper door 112 and compartment 108 when upper door 112 is closed to prevent the disinfectant solution from escaping from interior chamber 110 into the ambient air. Upper door 112 can also include a sensor (not shown) that automatically shuts off the disinfecting apparatus 100 when upper door 112 is opened.

An outer surface 114 of the lower portion 106 of the disinfecting apparatus 100 includes a plurality of support structures 116, shown in FIGS. 2-5 and 12, to support the disinfecting apparatus 100 on a horizontal, planar surface. Additionally, the disinfecting apparatus 100 can also include a mounting system 118 (not shown), located on an outer surface of a rear wall 120, shown in FIGS. 3-5, 8-12, and 17A, of the disinfecting apparatus 100, that is configured to secure the disinfecting apparatus 100 to a vertical, planar surface. Rear wall 120 also includes a female electrical connector 121 (FIG. 17A) that receives a power source, generally from a male electrical connector (not shown), to operate the disinfecting apparatus 100.

The top portion 102, shown in detail in FIGS. 6, 7, 7A-7E, and 18-20, of the disinfecting apparatus 100 comprises a top lid 122 and a bottom lid 124 that are attached to each other by a plurality of hinges 129. The top portion 102 further comprises a locking mechanism 148 that secures the top lid 122 to the bottom lid 124, where the top lid 122 and the bottom lid 124 define a top chamber 126. The top lid 122 of the top portion 102 is configured to pivot or rotate upward about the plurality of hinges 129 when the locking mechanism 148 is not engaged, to allow access to the top chamber 126. The top lid 122 can also be removed from the bottom lid 124 of the top portion 102 by removing the plurality of hinges 129 for maintenance or cleaning of the top lid 122 and/or the top chamber 126. The top portion 102 is attached to the upper portion 104 by a plurality of hinges 131 that allow the top portion 102 to be opened to provide access to the interior chamber 110 of the upper portion 104 of the disinfecting apparatus 100. The plurality of hinges 131 can comprise friction hinges configured to maintain the top portion 102 open and maintain access to the interior chamber 110. The top portion 102 further comprises two sealing gaskets 156 (FIG. 7), 158 (FIGS. 5, 8-10). Sealing gasket 156 forms a seal between the top lid 22 and the bottom lid 124, thereby sealing the top chamber 126 of the disinfecting apparatus 100. Sealing gasket 158 forms a seal between the bottom lid 124 of the top portion 102 and the upper portion 104 of the disinfecting apparatus 100, thereby sealing the interior chamber 110 of the upper portion 104.

Figure 6:
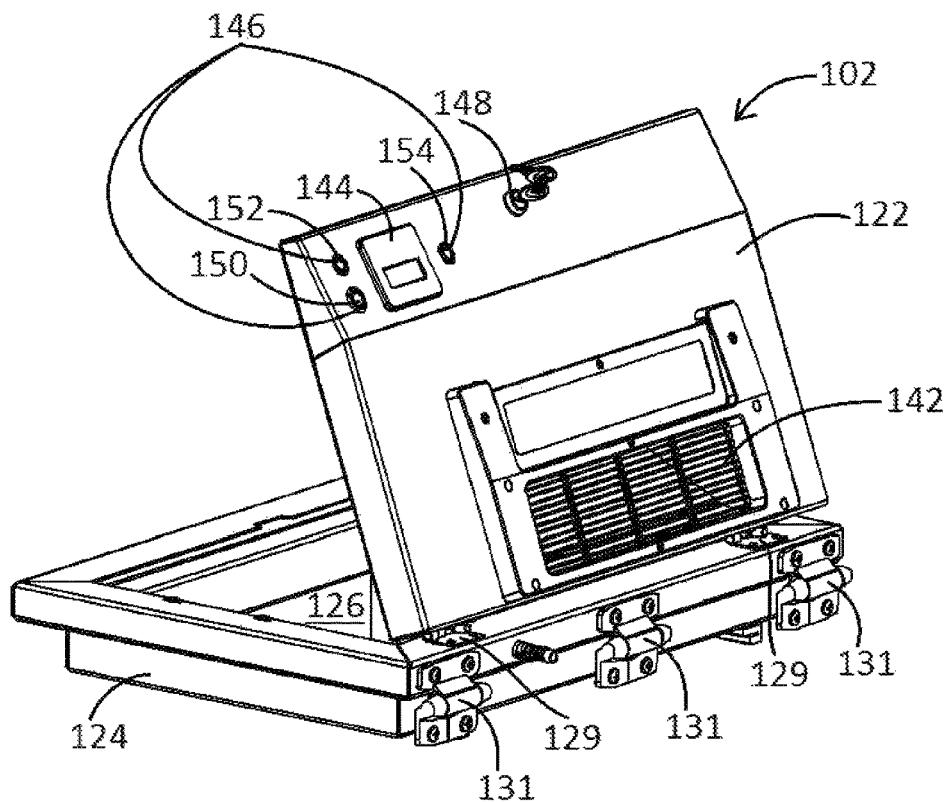
FIG. 6 is a rear second side perspective view of the top portion of the second embodiment of the disinfecting apparatus, shown with the top portion open.
Figure 7:
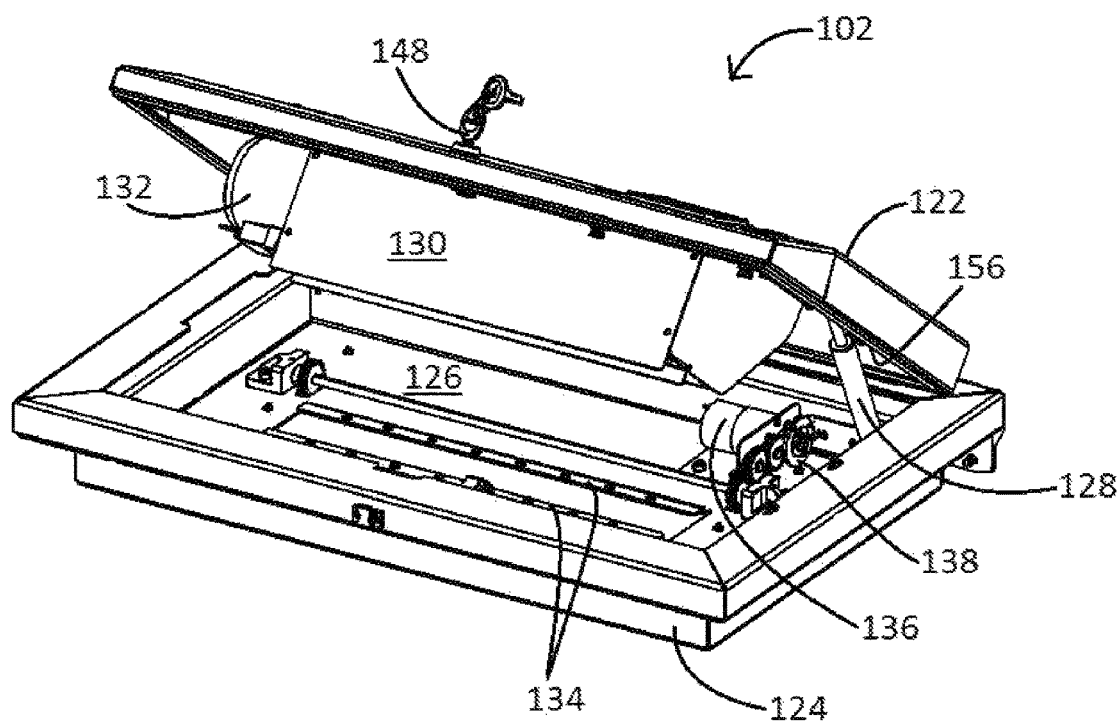
FIG. 7 is a front second side perspective view of the top portion of the second embodiment of the disinfecting apparatus, showing a plurality of top inner components of the top portion.
Figure 7A:
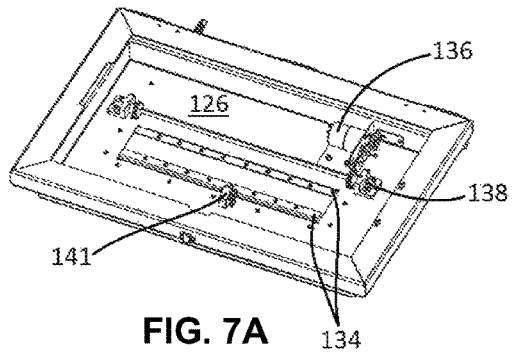
FIG. 7A is a top perspective view of a top chamber of the top portion of the second embodiment of the disinfecting apparatus, showing the plurality of top inner components of the top portion.
Figure 7C:
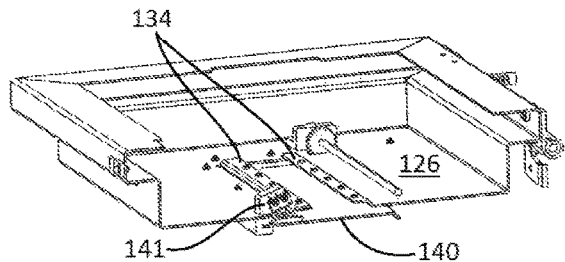
FIG. 7C is a cross-sectional side perspective view of the top chamber of the top portion of the second embodiment of the disinfecting apparatus, showing a gate sensor.
Figure 7B:
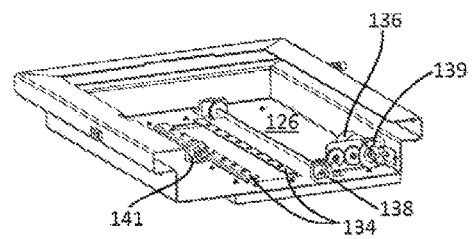
FIG. 7B is a cross-sectional side perspective view of the top chamber of the top portion of the second embodiment of the disinfecting apparatus, showing the plurality of top inner components of the top portion.
Figure 7E:
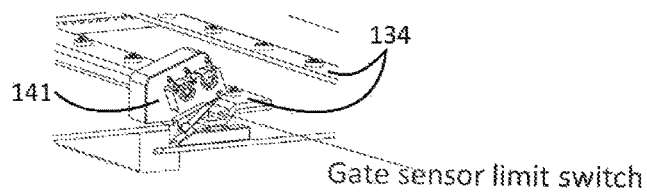
FIG. 7E is a cross-sectional detail side perspective view of top chamber of the top portion of the second embodiment of the disinfecting apparatus, showing the gate sensor of FIG. 7C.
Figure 7D:
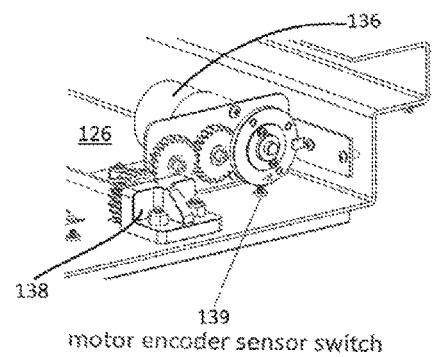
FIG. 7D is a cross-sectional detail side perspective view of top chamber of the top portion of the second embodiment of the disinfecting apparatus, showing a motor and a gear reduction mechanism.
Figure 8:
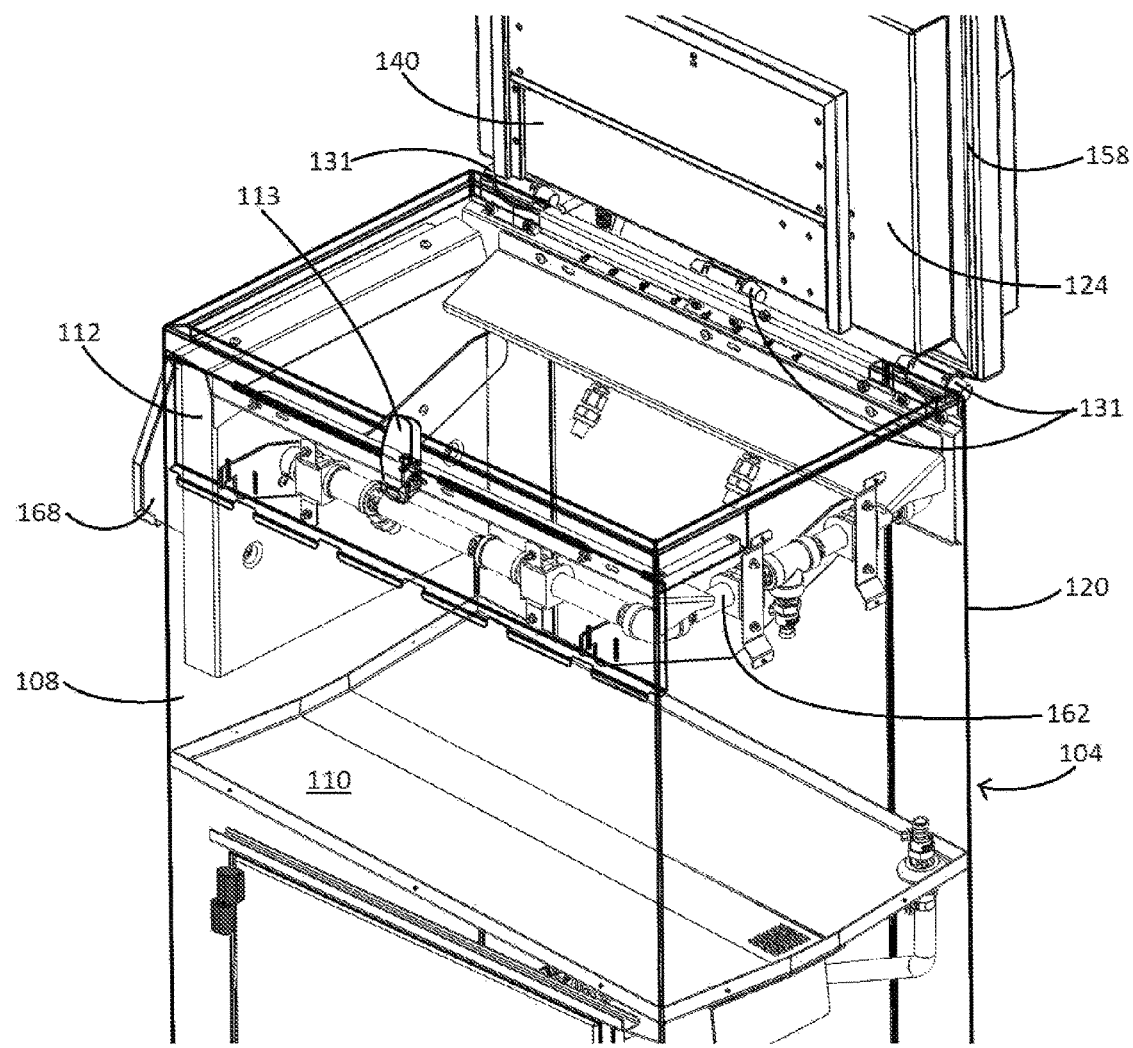
FIG. 8 is a front second side detail perspective view of the upper portion of the second embodiment of the disinfecting apparatus with the top portion open, showing a skeletal view of the upper portion of the disinfecting apparatus to show the plurality of inner components of the upper portion, comprising a plurality of jets.

Referring to FIG. 6, the top lid 122 of the top portion 102 of the disinfecting apparatus 100 comprises an air vent 142, a light indicator panel 144, and a plurality of switches 146. In this second embodiment, the plurality of switches 146 include a start switch 150, a stop or kill switch 152, and a reset switch 154. Other modifications of this second embodiment can include additional or alternative switches. The light indicator panel 144 can, in this embodiment, comprise a liquid crystal display that discloses various statuses of the disinfecting apparatus 100, such as, for example, an on or off status, a washing status, a rinsing status, a low liquid status, a change liquid status, a time remaining status alerting the user of the time remaining in the cycle of operation, and a cycle complete status. The light indicator panel 144 can also be equipped with an audio component (not shown) that produces a sound when a certain status has been detected, such as beeping when a cycle of operation has been completed or when the disinfectant solution needs to be replaced. Additionally, other modifications of this second embodiment can include a timer that will maintain the disinfecting apparatus 100 closed, locked, and/or sealed for a predetermined amount of time while the disinfecting apparatus 100 is in a cycle of operation.

Figure 14A:
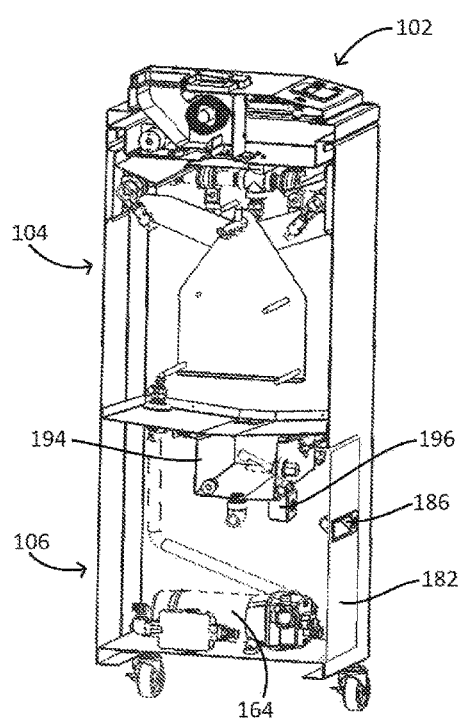
FIG. 14A is a cross-sectional first side perspective view of the second embodiment of the disinfecting apparatus, showing the top portion, the upper portion, and the lower portion of the disinfecting apparatus.
Figure 14B:
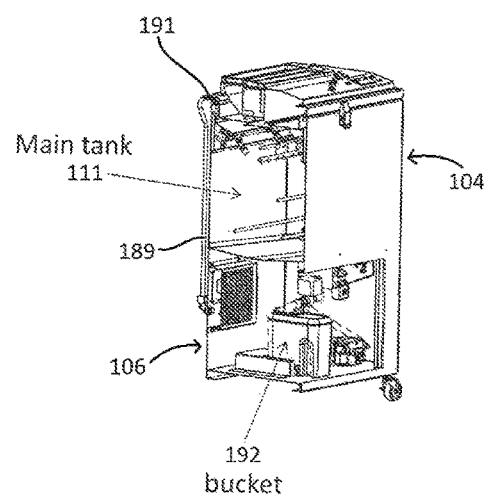
FIG. 14B is a cross-sectional first side perspective view of the second embodiment of the disinfecting apparatus, showing the top portion, the upper portion, and the lower portion of the disinfecting apparatus.
Figure 14C:
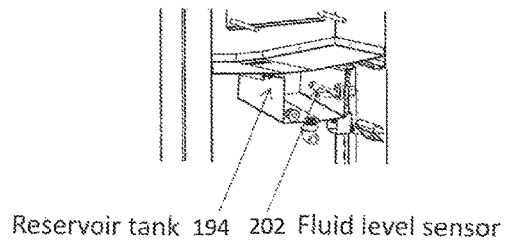
FIG. 14C is a front first side cross-sectional detail perspective view of the lower portion of the second embodiment of the disinfecting apparatus, showing a reservoir tank of the lower portion in a closed position.
Figure 18:
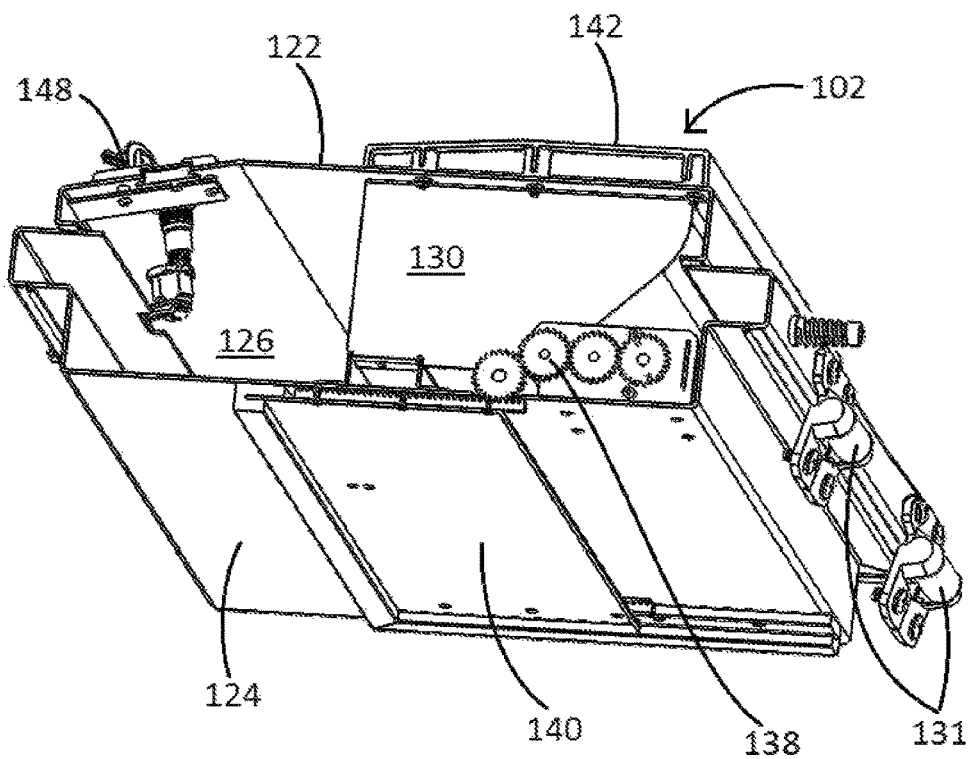
FIG. 18 is a second side cross-sectional perspective view of the top portion of the second embodiment of the disinfecting apparatus, showing a short wavelength ultraviolet (UV-C) light door in a closed position.
Figure 19:
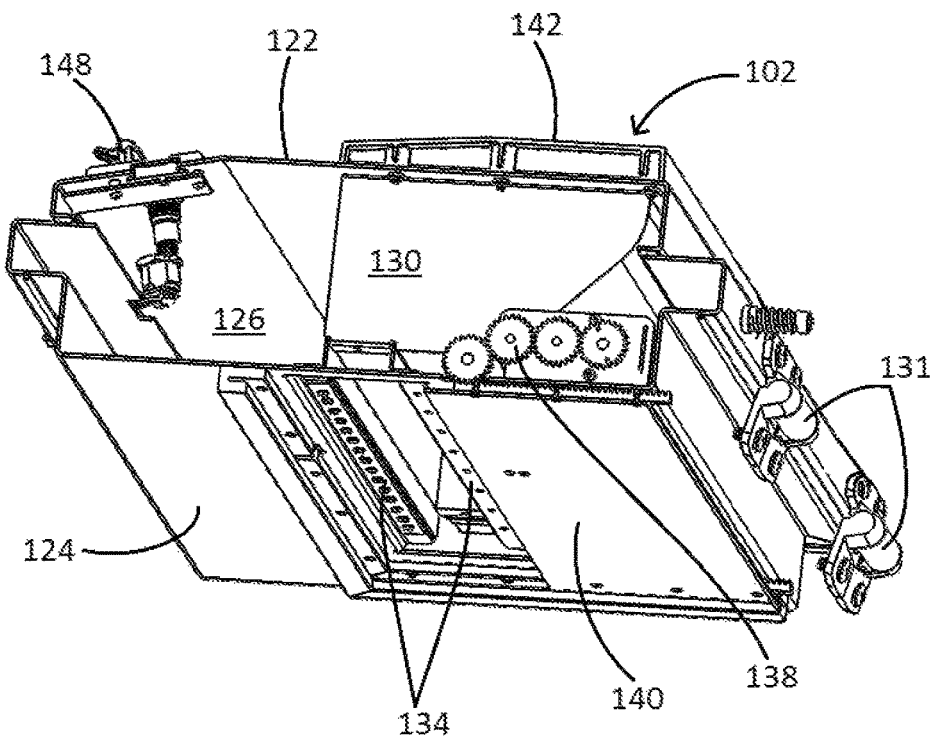
FIG. 19 is a second side cross-sectional perspective view of the top portion of the second embodiment of the disinfecting apparatus, showing the UV-C light door in an open position.
Figure 20:
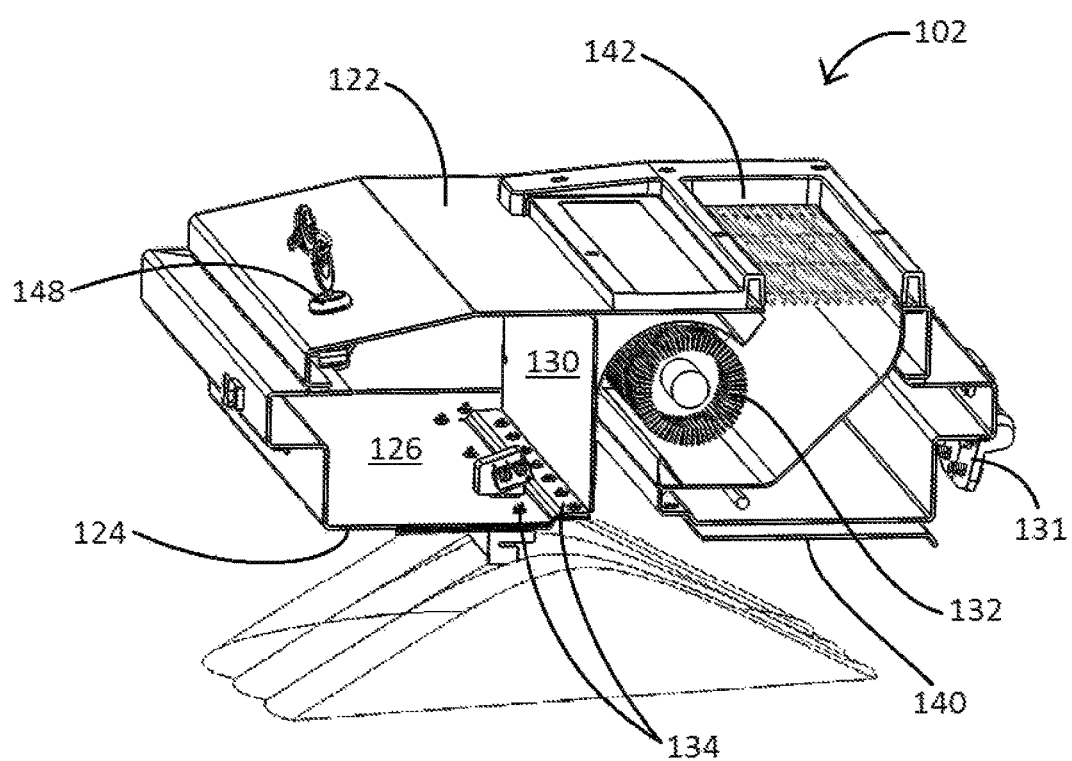

The top chamber 126 comprises a piston and cylinder opening mechanism 128 (FIG. 7) that causes the top lid 122 to open upwards about the hinges 129 to provide access to the top chamber 126 for maintenance and to control the speed in which the top lid 122 is lowered to close access to the top chamber 126. As shown in FIGS. 7 and 18-20, the top chamber 126 further comprises at least one plenum 130 that receives and distributes air from a blower 132 and a plurality of UV-C lights 134, that are exposed to the interior chamber 110 of the upper portion 104 when a motor 136 that operates a gear reduction mechanism 138 is configured to move a UV-C access panel door 140 (FIGS. 2-5, 7C, 8, 10, 18, and 20) located on the bottom lid 124, thereby exposing the UV-C lights 134 to the interior chamber 110, as shown in FIGS. 19 and 20. This UV-C access panel door 140 includes a gate sensor 141 (FIGS. 7B, 7C, and 7E) that detects when the UV-C access panel door 140 is not open and is configured to prevent the UV-C panel door 140 from opening until the interior chamber 110 has eliminated all the disinfectant solution from then main tank 202 (FIG. 14B). If the gate sensor 141 detects that the UV-C panel door 140 is open, the disinfecting apparatus will not operate.

A motor encoder sensor switch 139 (FIGS. 7A, 7B, 7D) activates the motor 136 that activates the gear reduction mechanism 138 to open and fully close the UV-C access panel door 140. After the disinfectant solution has cleared from the interior chamber 110 and main tank 111, the UV-C access panel door 140 of the bottom lid 124 is fully opened by the gear reduction mechanism 138, allowing air from the blower 132 and UV-C light from the plurality of UV-C lights 134 to be exposed to the items within the interior chamber 110 of the upper portion 104, as shown in FIGS. 18-20.

Figure 9:
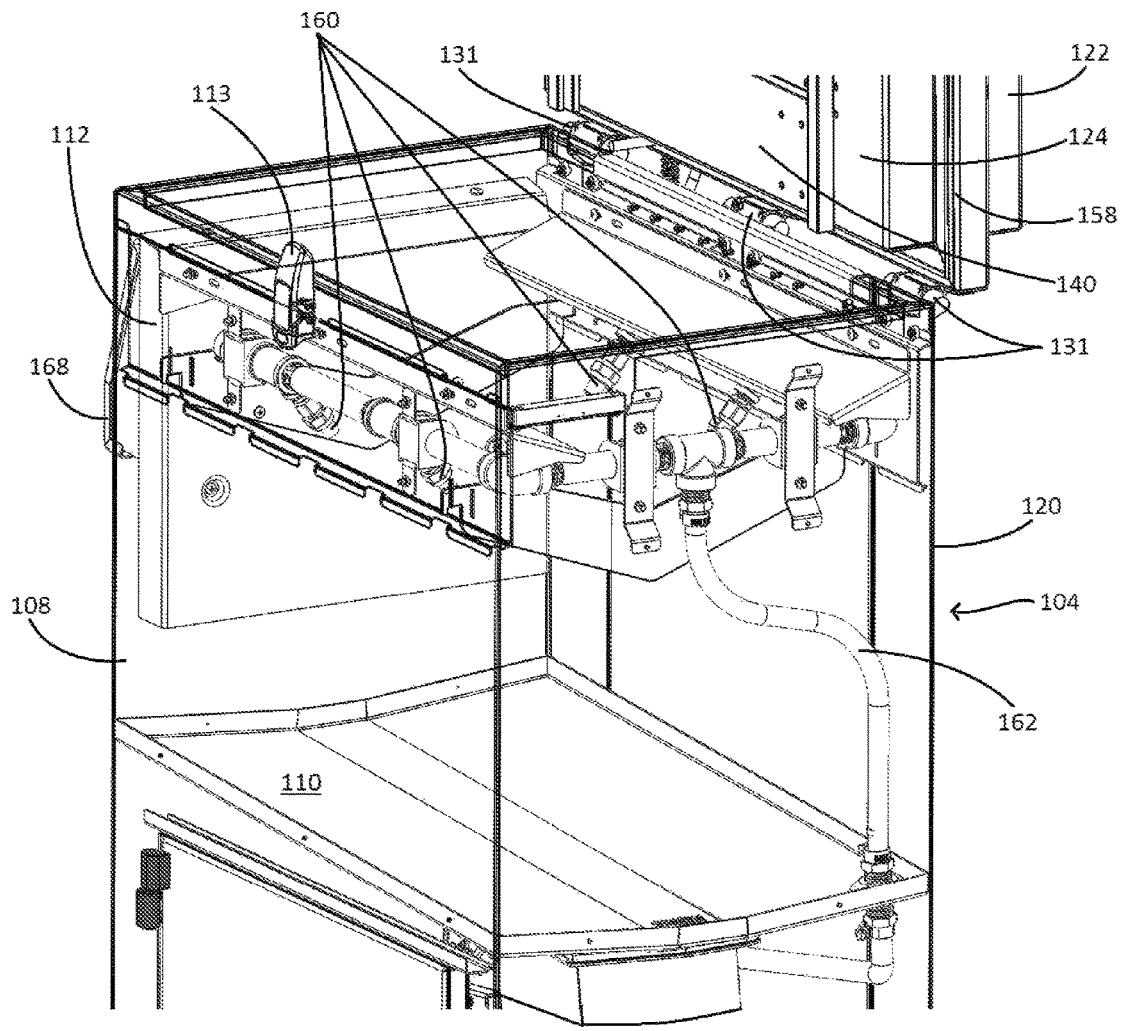
FIG. 9 is a front second side detail perspective view of the upper portion of the second embodiment of the disinfecting apparatus with the top portion open, showing a skeletal view of the upper portion of the disinfecting apparatus to show the plurality of inner components of the upper portion and the plurality of jets in the upper portion in connection with the lower portion.
Figure 10:
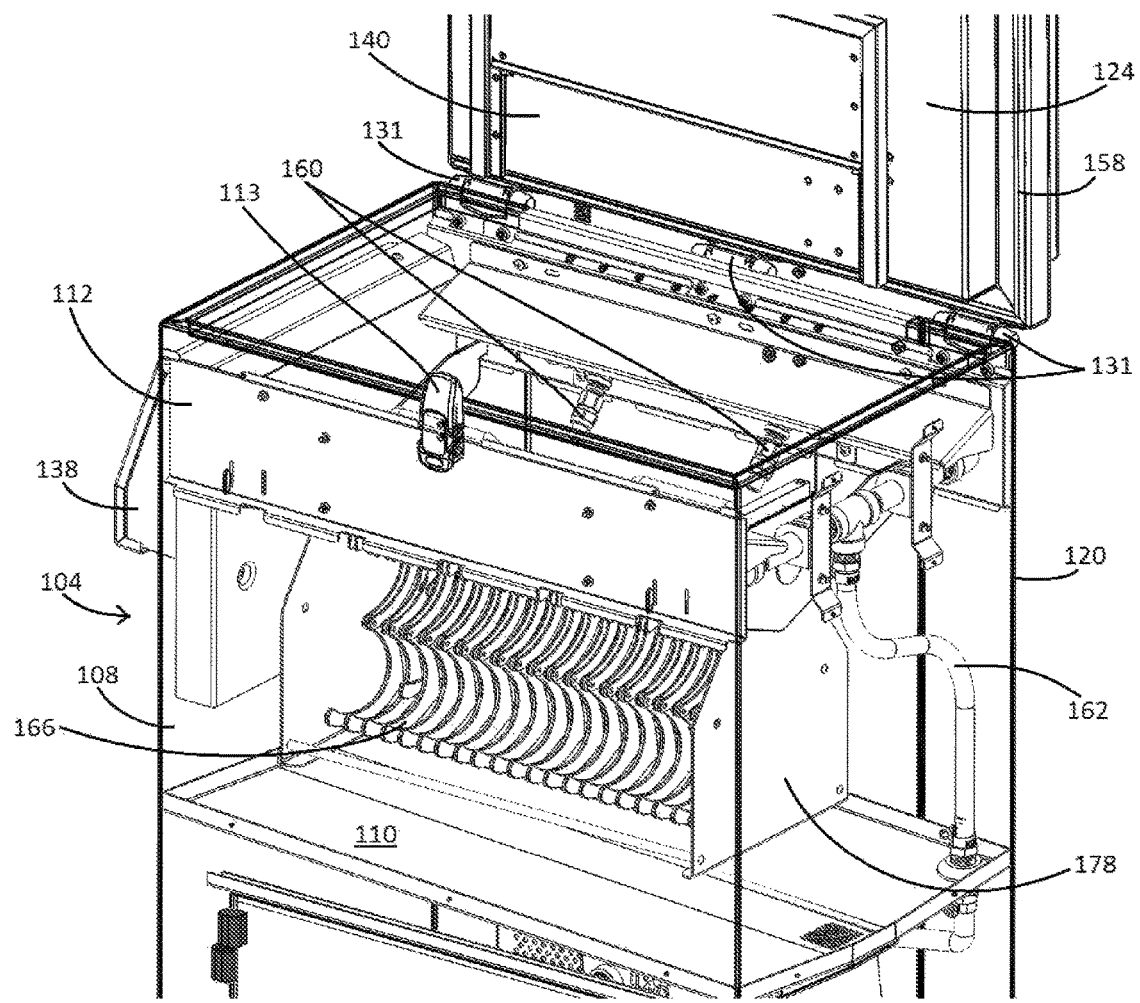
FIG. 10 is a front second side detail perspective view of the upper portion of the second embodiment of the disinfecting apparatus with the top portion open, showing a skeletal view of the upper portion of the disinfecting apparatus to show at least one removable holding device in the upper portion.

The disinfecting apparatus 100 also comprises a plurality of jets 160 (FIGS. 2-4 and 8-11) on a piping system 162 (FIG. 9) that is disposed in the interior chamber 110 of the upper portion 104. The piping system 162, which includes at least two nozzles on each side as shown in FIG. 9, provides substantially even pressure to each individual jet in the plurality of jets 160 connected to that piping system 162. The water pump 164 (FIGS. 12 & 13) conveys the disinfectant solution to the interior chamber 110 through piping system 162 and the plurality of jets 160. The plurality of jets 160 then conveys the disinfectant solution in a pulsed spray or a continuous mist spray to the devices 166 within interior chamber 110 of compartment 108 to be cleaned. The plurality of jets 160 can also include stainless steel tips.

Figure 2:
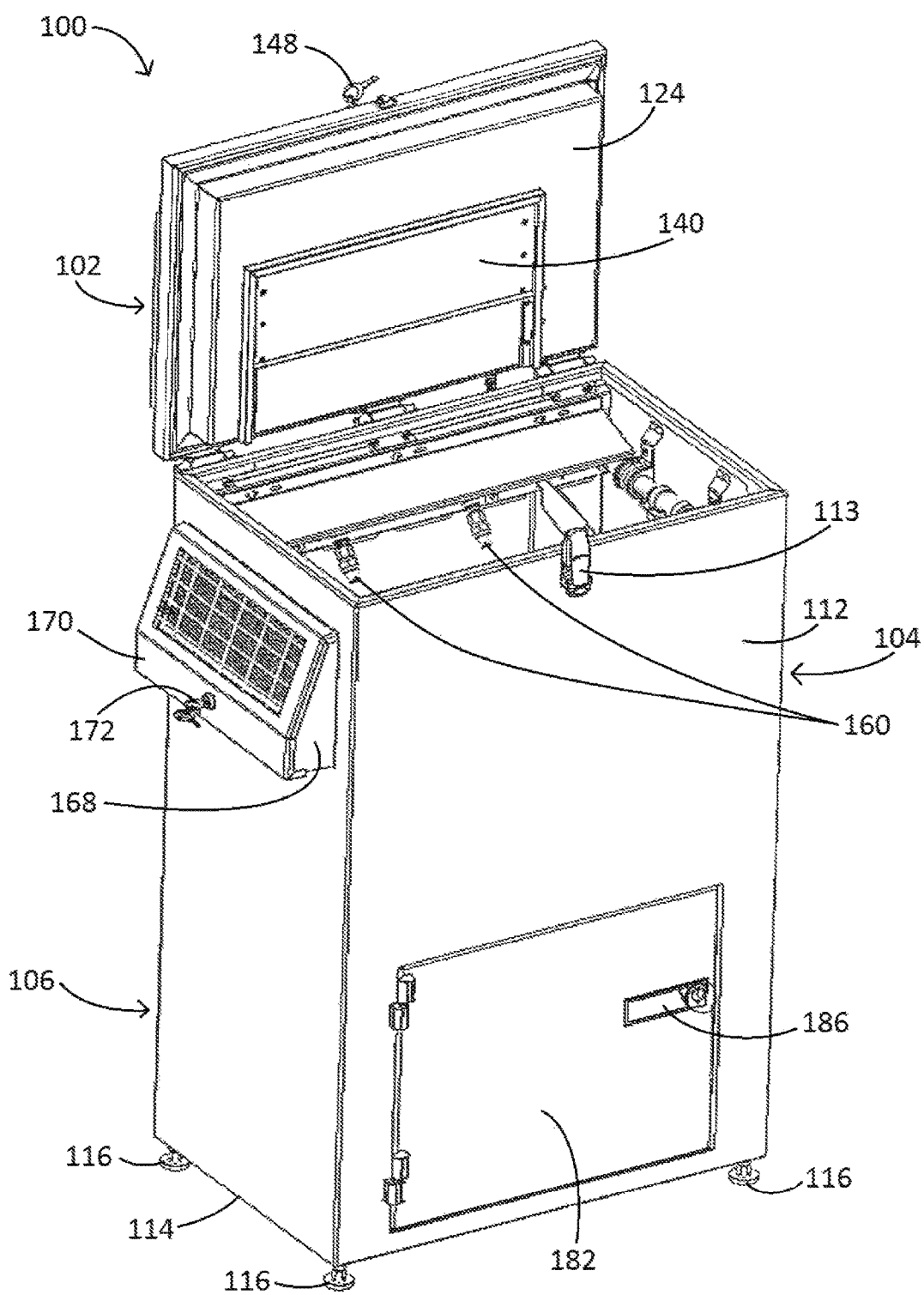
FIG. 2 is a front first side perspective view of a second embodiment of the disinfecting apparatus, shown with a top portion open.
Figure 3:
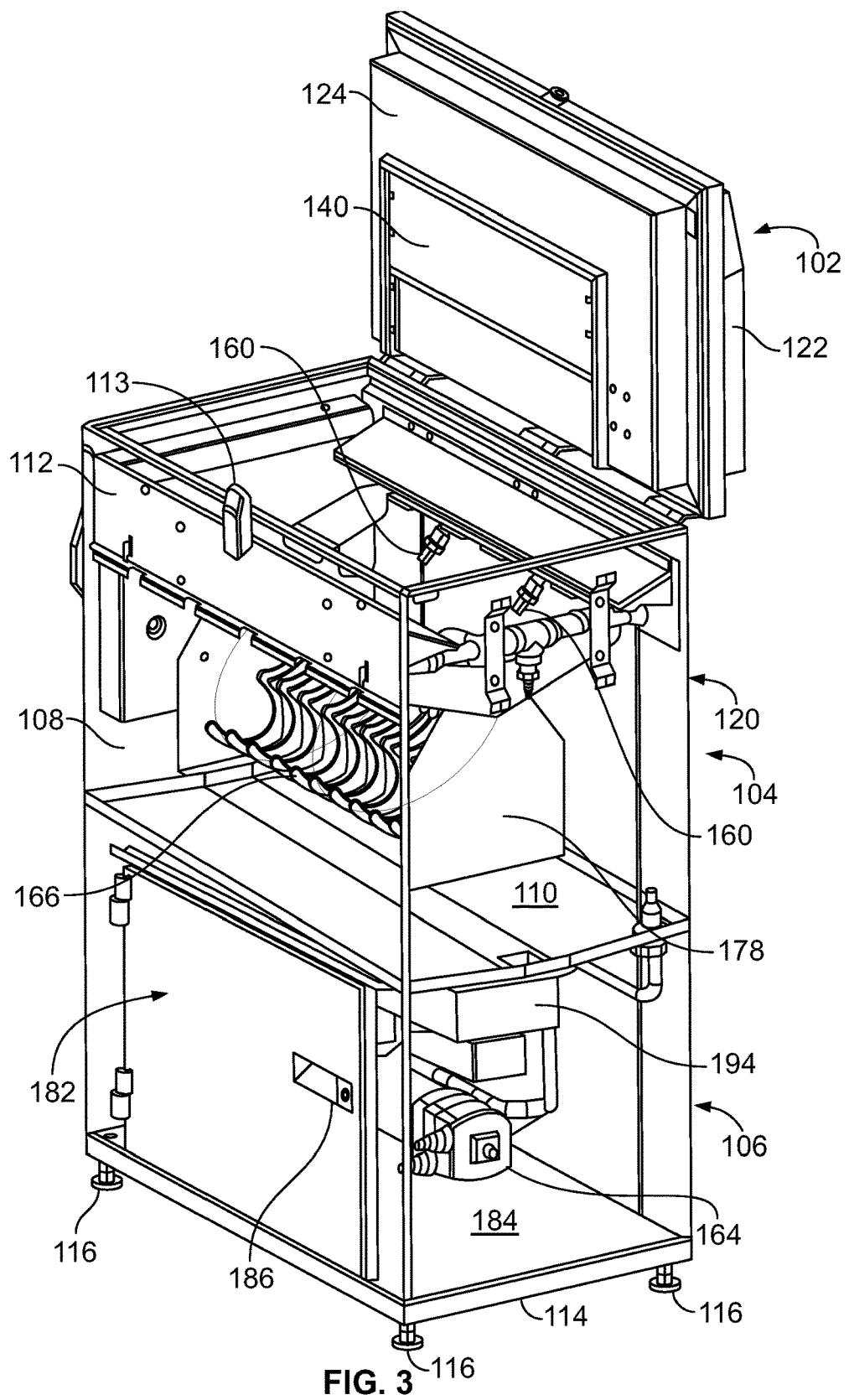
FIG. 3 is a front second side perspective view of the second embodiment of the disinfecting apparatus with the top portion open, showing the disinfecting apparatus in skeletal view to show a plurality of inner components of the disinfecting apparatus.
Figure 4:
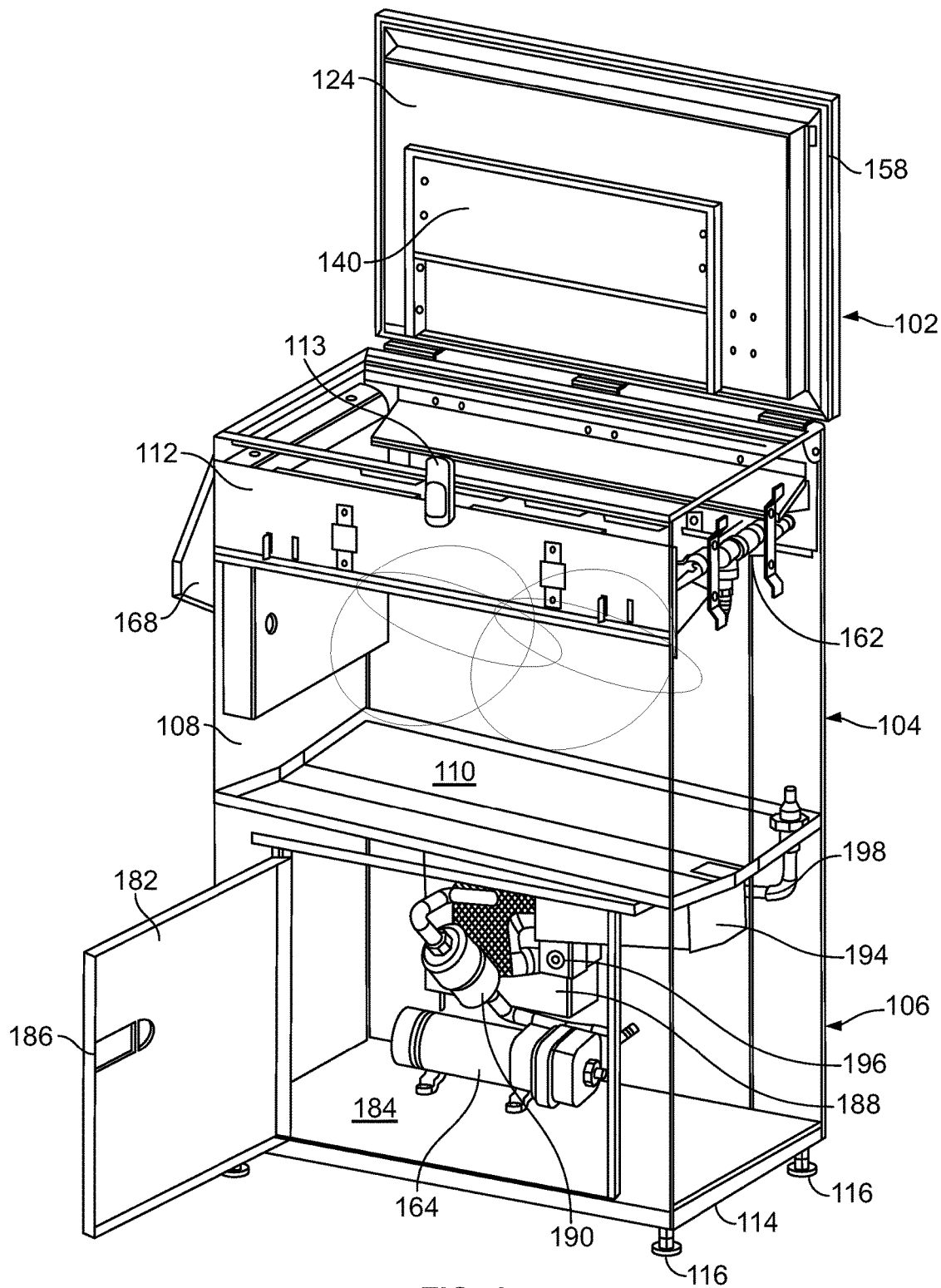
FIG. 4 is a front second side perspective view of the second embodiment of the disinfecting apparatus with the top portion open, shown with a door open of a lower portion of the disinfecting apparatus to show a plurality of lower inner components of the lower portion, and showing a skeletal view of an upper portion of the disinfecting apparatus to show a plurality of upper inner components of the upper portion.
Figure 5:
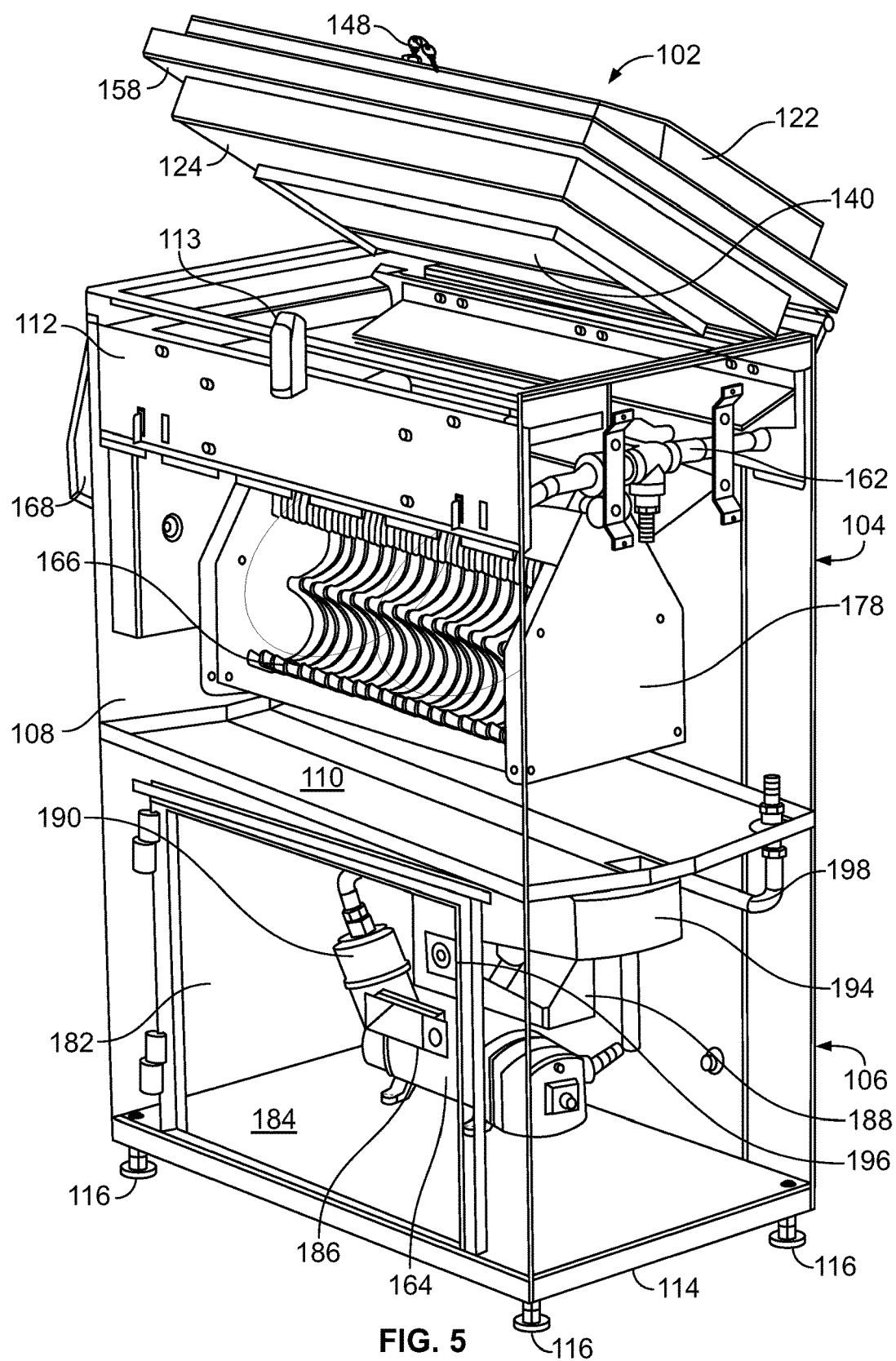
FIG. 5 is a front second side perspective view of the second embodiment of the disinfecting apparatus with the top portion partially open, showing the upper portion and the lower portion of the disinfecting apparatus in skeletal view to show the plurality of components.
Figure 11:
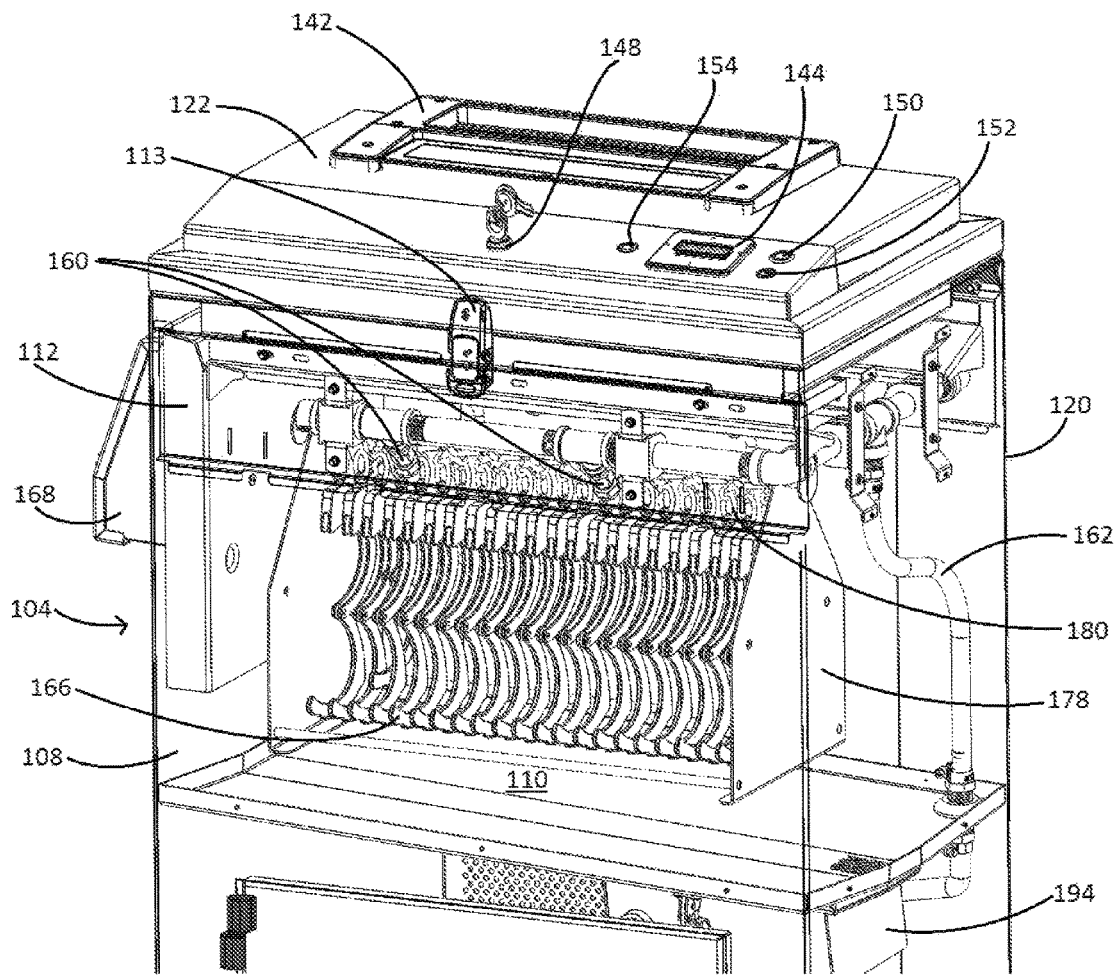
FIG. 11 is a front second side detail perspective view of the upper portion of the second embodiment of the disinfecting apparatus with the top portion closed, showing a skeletal view of the upper portion of the disinfecting apparatus to show the plurality of jets and the at least one removable holding device holding a plurality of items in the upper portion.

The disinfecting apparatus 100 includes a filtration system housing 168 that includes an access door 170 with a locking mechanism 172 that secures the access door 170 to the filtration system housing 168, as shown in FIGS. 2 and 11. Access door 170 can be opened for maintenance and to replace the filtration system filter 174 (FIGS. 16A-16C) contained within the filtration system housing 168 configured to prevent and deter chemical and air from escaping the disinfecting apparatus 100. In this illustrated embodiment, the filtration system filter 174 includes an air filter 176 (FIG. 16A), such as quadrafoam, that features open cell polyurethane foams specially coated to provide improved flame, fungus, and UV radiation resistance, or other hydrophobic mesh filters, which filter moisture and protect the water pump 164 and plurality of jets 160, and a charcoal filter 177 (FIG. 16A) that filters the air to rid the air of unwanted odors. The air filter 176 and the charcoal filter 177 are held together within a filter pack frame 179 (FIG. 16A) which together forms the filtration system filter 174 (FIG. 16B), which is configured to provide a pleasant scent in the ambient air outside the disinfecting apparatus 100, to control moisture within the interior chamber 110, and/or to keep the disinfectant solution and air inside the compartment 108. In this particular embodiment, for illustration purposes only, the filtration system filter 174 is shown in particular orientations and dimensions, as shown in FIG. 16C.

The interior chamber 110 of the compartment 108 includes a removable holding device 178, shown in FIGS. 3, 5, and 10-12, that includes the plurality of support structures 180 (FIG. 11), such as hooks, that are configured to hold at least one device 166 per support structure 180 and to allow the disinfecting apparatus 100 to potentially clean a plurality of devices 166 at one time. In one embodiment, the removable holding device 178 may not have a floor, allowing devices 166 to hang freely. In another embodiment, the removable holding device 178 may include a floor (not shown) to allow users to place devices 166 on the floor to be cleaned. In yet another embodiment, the removable holding device 178 may include a motor to provide motorized rotation of the removable holding device 178.

The lower portion 106 of the disinfecting apparatus 100, shown in FIGS. 2-5, 12, and 13, further comprises a lower door 182 that provides access to a lower chamber 184. The lower door 182 includes a locking mechanism 186 that secures the lower door 182 to the lower portion 106. The lower chamber 182 houses the water pump 164, an electronics component 188, a filter 190, a rotatable reservoir tank 194, and a sewage check valve 196. The electronics component 188 is connected to the top portion 102 through cabling or connector 189, as shown in FIGS. 14B, 17B, and 17C, and the top portion 102 includes a strain relief 191 that attaches to connector 189. The sewage check valve 196 closes to prevent the backward flow of disinfectant solution from the water pump 164 to the rotatable reservoir tank 194.

In one embodiment, shown in FIGS. 14A-14C and 15, the lower portion 106 further includes a bucket 192 (FIGS. 14B and 15) that collects disinfectant solution that is no longer suitable for disinfectant use in the disinfecting apparatus 100 from the reservoir tank 194. The bucket 192 can be removed from the lower portion 106 and emptied when it has reached capacity. In this embodiment, the lower portion 106 also includes a bucket sensor (not shown) that detects when the bucket 192 has been removed and prevents the reservoir tank 194 from disposing disinfectant solution from the reservoir tank 194 into the bucket 192.

Figure 12:
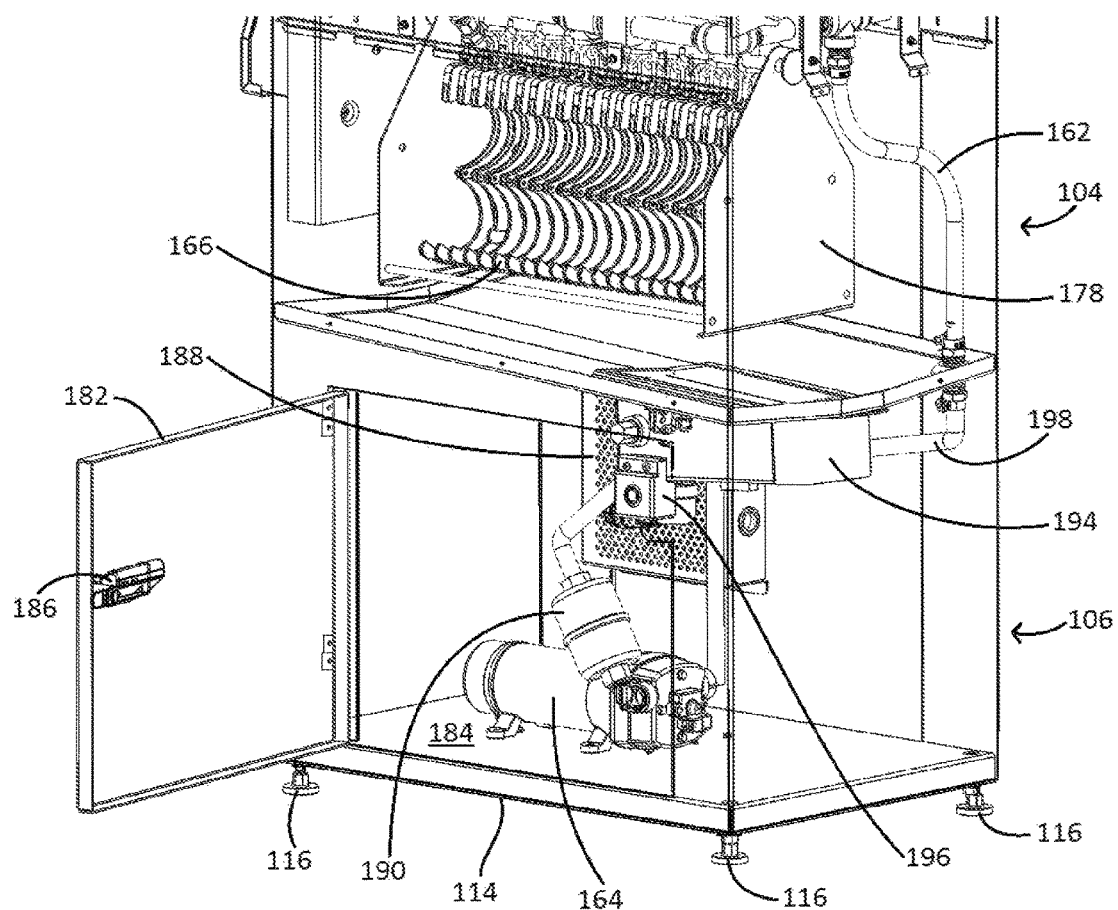
FIG. 12 is a front second side detail skeletal perspective view of the lower portion of the second embodiment of the disinfecting apparatus, shown with a lower door open of the lower portion to show the plurality of lower inner components of the lower portion with a removable collection tray in a closed position.
Figure 13:
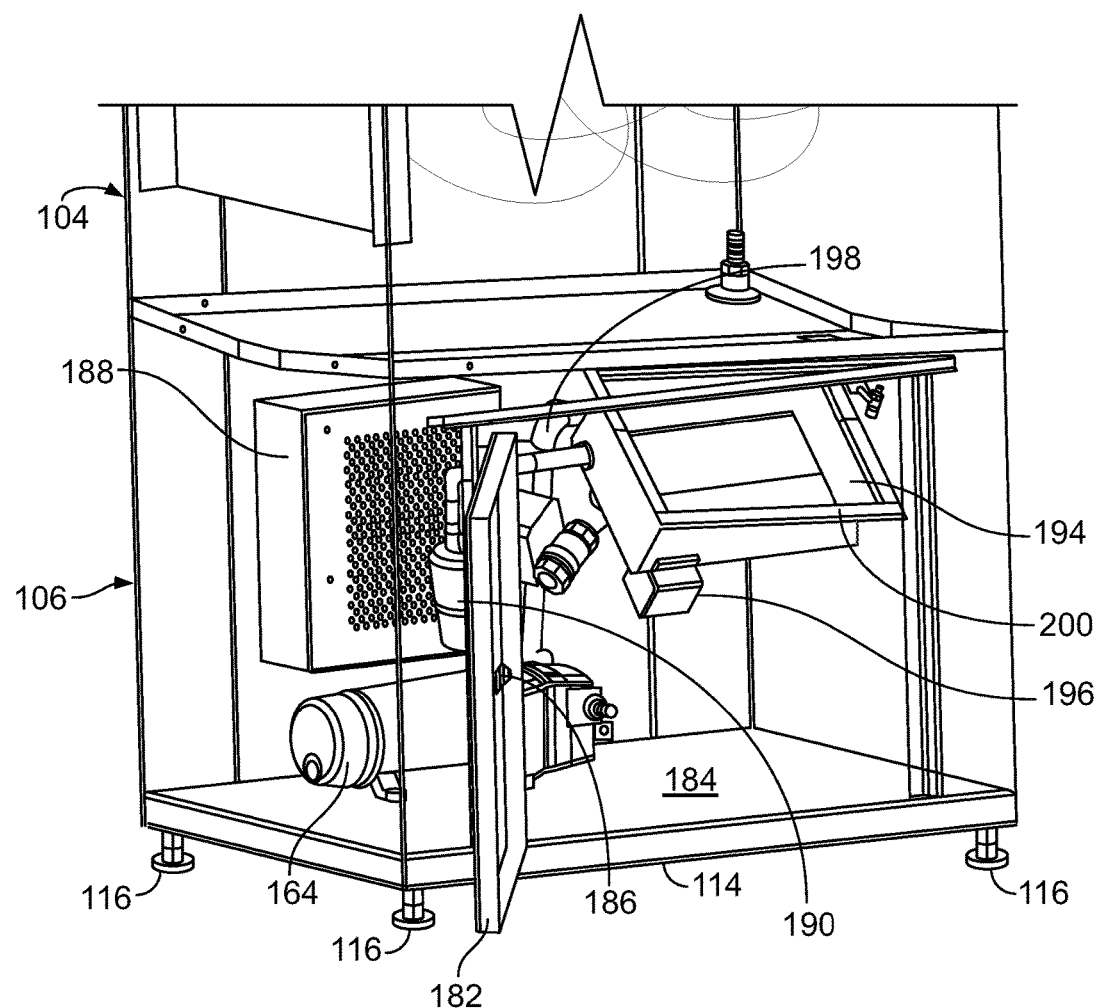
FIG. 13 is a front first side detail skeletal perspective view of the lower portion of the second embodiment of the disinfecting apparatus, shown with the lower door open of the lower portion to show the plurality of lower inner components of the lower portion with the removable collection tray in an open, cleaning position.
Figure 14D:
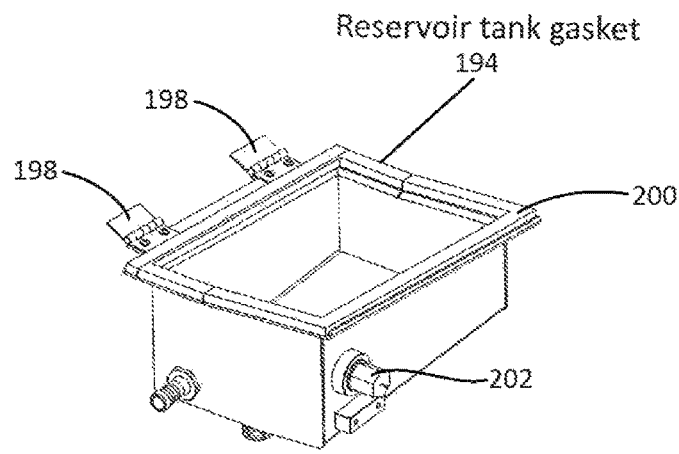
FIG. 14D is a detail perspective view of the reservoir tank of the second embodiment of the disinfecting apparatus.
Figure 15:
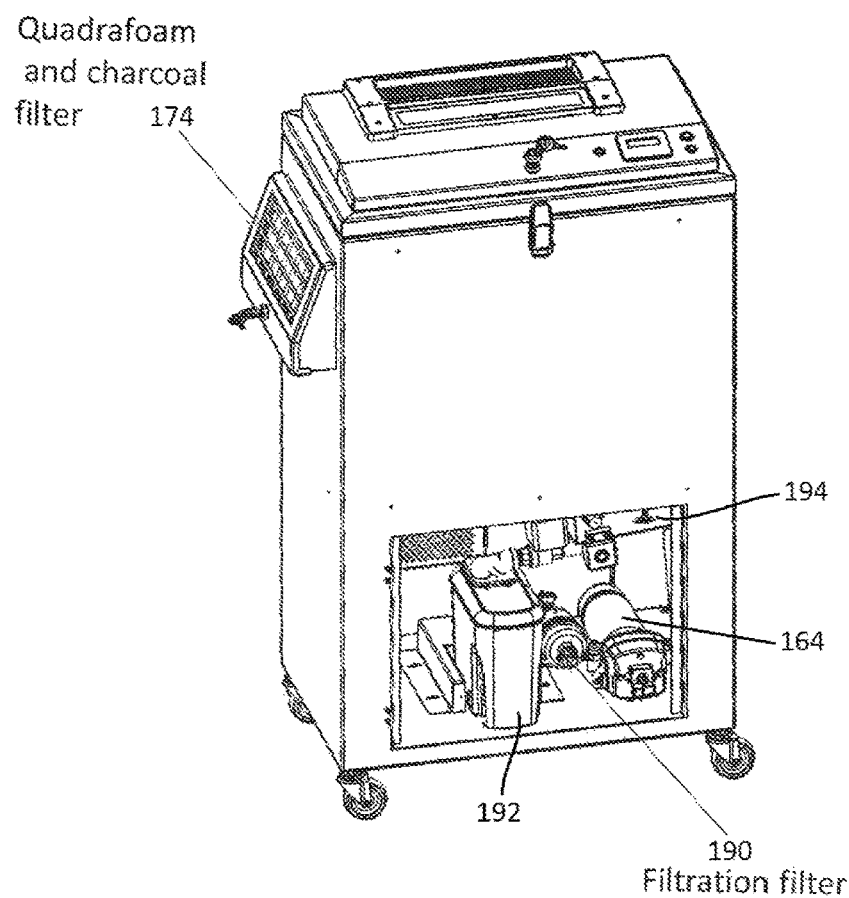
FIG. 15 is a front perspective view of the second embodiment of the disinfecting apparatus, showing the lower door of the lower portion open.

The rotatable reservoir tank 194, shown in detail in FIG. 14D, includes a fluid level sensor 202 (FIG. 14C) that detects the fluid level of disinfectant solution in the reservoir tank 194 and determines when the reservoir tank 194 needs to be emptied. The fluid level sensor 202 also prevents the disinfecting apparatus 100 from operating when the fluid level of the disinfectant solution within the reservoir tank 194 is below a predetermined threshold detected by the fluid level sensor 202. Pivotal hinges 198 and a sealing gasket 200 (FIG. 13, 14D) hold the reservoir tank 194 secured in place as shown in FIG. 12. A motorized drain valve (not shown) is activated to empty the reservoir tank 194. The rotatable reservoir tank 194 can be pivoted down along pivotal hinges 198, as shown in FIG. 13, for cleaning or the reservoir tank 194 can be removed from the lower portion 106 for cleaning.

To disinfect a plurality of devices 166, the user places the devices 166 in the removable holding device 178 and closes and locks the top portion 102 and the upper door 112 to seal the interior chamber 110. When the disinfecting apparatus 100 is in a cycle of operation, a predetermined amount of disinfectant solution is poured into the main tank 111 (FIG. 14B) which will automatically flow into the rotatable reservoir tank 194 after the disinfectant solution has been used. The water pump 164 conveys the disinfectant solution from the reservoir tank 194 through filter 190 (FIG. 15), which prevents the plurality of jets 160 from clogging, to the piping system 162 that delivers the disinfectant solution to the plurality of jets 160 to clean, disinfect, sanitize, and sterilize the devices 166 located in the removable holding device 178. The plurality of jets 160 provide a pulsed spray or a continuous mist spray of the disinfectant solution to the devices 166 within interior chamber 110. During the disinfectant solution dispensing and sanitation cycle, the UV-C access panel door 140 of the bottom lid 124 remains closed, as shown in FIG. 18, to protect and keep the blower 132 and plurality of UV-C lights 134 dry.

Once the disinfectant solution has fully run through the piping system 162 and plurality of jets 160 and the disinfectant solution stage has ended, the gear reduction mechanism 138 opens the UV-C access panel door 140, as shown in FIG. 19, to expose the blower 132 and the plurality of UV-C lights 134 to the interior chamber 110 of the compartment 108 of the upper portion 104. In the final stage, the blower 132 blows air onto the devices 166 and the plurality of UV-C lights 134 shine UV-C light, as shown in FIG. 20, onto the devices 166 to further disinfect, sanitize, and sterilize the devices 166. After the blower 132 has run and the UV-C lights 134 sterilization has completed, the top portion 102 and/or upper door 112 can be opened to remove the sterilized devices 166.

While the present disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A disinfecting apparatus for cleaning at least one device, the disinfecting apparatus comprising:
    an upper portion comprising a compartment that defines an interior chamber, the upper portion having a top portion in moveable communication with the upper portion, the top portion configured to alternately open and close access to the interior chamber;
    an upper door in moveable communication with the compartment, the upper door configured to alternately open and close access to the interior chamber;
    a plurality of jets disposed in the upper portion, the plurality of jets configured to convey a disinfectant solution from a disinfectant chamber to the interior chamber;
    a lower portion subjacent the upper portion, the lower portion comprising a lower door, a lower chamber, a rotatable tray, and a water pump configured to convey the disinfectant solution from the disinfectant chamber to each jet of the plurality of jets with an equal pressure to each jet, the lower door in moveable communication with the lower portion, the lower door configured to alternately open and close access to the lower chamber.

2. The disinfecting apparatus of claim 1, further comprising:
    a top lid opposite a bottom lid that define a top chamber of the top portion, the top lid in moveable communication with the top portion and configured to alternately open and close access to the top chamber, and the bottom lid in moveable communication with the upper portion and configured to alternately open and close access to the interior chamber;
    at least one of a blower and at least one plenum disposed in the top chamber, the blower configured to provide air to the at least one device;
    a plurality of short-wavelength ultraviolet (UV-C) lights disposed on the bottom lid; and
    a UV-C access panel in moveable communication with the bottom lid, the UV-C access panel comprising a gate sensor configured to prevent the UV-C access panel from opening until the upper portion has eliminated all the disinfectant solution from the disinfectant chamber, and the UV-C access panel configured to expose the plurality of UV-C lights to the at least one device in the interior chamber.

3. The disinfecting apparatus of claim 2, further comprising:
    a first sealing gasket disposed in the top portion, the first sealing gasket configured to form a seal between the top lid and the bottom lid; and
    a second sealing gasket disposed in the top portion, the second sealing gasket configured to form a seal between the bottom lid and the upper portion.

4. The disinfecting apparatus of claim 2, further comprising:
    a piston and cylinder opening mechanism configured to open the top lid and provide access to the top chamber.

5. The disinfecting apparatus of claim 2, further comprising:
    a gear reduction mechanism disposed in the top chamber, the gear reduction mechanism configured to move, open, and close, using a motor activated by a motor encoder sensor switch, the UV-C access panel and expose the plurality of UV-C lights to the interior chamber; and
    the motor disposed in the top chamber, the motor configured to selectively operate the gear reduction mechanism.

6. The disinfecting apparatus of claim 5, wherein the gear reduction mechanism is configured to slidably move the UV-C access panel relative to the bottom lid.

7. The disinfecting apparatus of claim 5, wherein the UV-C access panel is slidably moveable to a plurality of locations along the bottom lid, the plurality of locations configured to expose at least one of the plurality of the UV-C lights.

8. The disinfecting apparatus of claim 2, further comprising:
    an outer top wall of the top lid, the outer top wall comprising an air vent.

9. The disinfecting apparatus of claim 8, further comprising:
    at least one light indicator disposed on the outer top wall, the at least one light indicator comprising at least one of a ready light indicator and a low disinfectant solution indicator;
    at least one power switch disposed on the outer top wall; and
    a timer disposed on the outer top wall.

10. The disinfecting apparatus of claim 9, wherein the timer is a liquid crystal display timer.

11. The disinfecting apparatus of claim 1, further comprising:
    a removable holding device disposed in the interior chamber, the removable holding device comprising a plurality of support structures configured to support the at least one device.

12. The disinfecting apparatus of claim 1, further comprising:
    a filter disposed on an outer wall of the upper portion; and
    an access panel enclosing the filter, the access panel comprising an access panel door in moveable communication with the access panel, the access panel door configured to alternately open and close access to the filter.

13. The disinfecting apparatus of claim 12, wherein the filter comprises an air filter and a charcoal filter.

14. The disinfecting apparatus of claim 13, wherein the air filter comprises a quadrafoam filter.

15. The disinfecting apparatus of claim 1, further comprising:
    a plurality of support feet disposed on an outer lower wall of the lower portion, the plurality of support feet configured to support the disinfecting apparatus on a planar surface.

16. The disinfecting apparatus of claim 1, wherein the compartment comprises a main tank configured to initially retain the disinfectant solution.

17. The disinfecting apparatus of claim 1, wherein the upper door comprises a sealing gasket configured to form a seal between the upper door and the compartment.

18. The disinfecting apparatus of claim 1, further comprising:
an electronics component disposed in the lower portion and connected to the top portion, the electronics component configured to operate the disinfecting apparatus.

19. The disinfecting apparatus of claim 18, further comprising:
a sensor configured to detect when the upper door is opened; and
wherein the electronics component is configured to shut off the disinfecting apparatus upon receiving a signal from the sensor indicating that the upper door is opened.

20. The disinfecting apparatus of claim 1, further comprising:
a piping system disposed in the upper portion, the water pump configured to convey the disinfectant solution from the rotatable tray to a filter disposed in the lower portion and to convey the disinfectant solution from the filter to the piping system, the piping system configured to convey the disinfectant solution to the plurality of jets, and the plurality of jets configured to convey the disinfectant solution in at least one of a pulsed spray, an intermittent spray, and a continuous spray to the interior chamber.

21. The disinfecting apparatus of claim 1, further comprising:
a fluid level sensor disposed in the rotatable tray, the fluid level sensor configured to detect the fluid level of the disinfectant solution in the rotatable tray and detect when the rotatable tray needs to be emptied;
a motorized drain valve configured to empty the rotatable tray;
a removable bucket disposed in the lower portion, the removable bucket configured to receive unusable disinfectant solution from the rotatable tray.

* * * * *